United States Patent [19]

Smidak

[11] 4,129,123

[45] Dec. 12, 1978

[54] DEFINED SPACE HAVING SOUND-INSULATED AND LIGHT-IMPERMEABLE WALLS, PREFERABLY INTENDED TO ENCLOSE A BED

[76] Inventor: Emil F. Smidak, 14 Chemin Hauts-Crets, 1223 Cologny, Switzerland

[21] Appl. No.: 838,406

[22] Filed: Sep. 30, 1977

[30] Foreign Application Priority Data

Oct. 1, 1976 [SE] Sweden ................................ 7610896

[51] Int. Cl.$^2$ ........................ F24F 9/00; A61B 19/00

[52] U.S. Cl. .................................. 128/1 R; 272/8 R; 109/1 S

[58] Field of Search ................ 52/29, 169.6, 236, 429, 52/27, 79.11; 5/105 , 284, 362; 109/1 5, 1 V; 128/1 R, 1 B, 204, 371 R, 402; 272/84; 35/25

[56] References Cited

U.S. PATENT DOCUMENTS

| | | | |
|---|---|---|---|
| 3,156,932 | 11/1964 | Mautner | 5/109 |
| 3,212,220 | 10/1965 | Boniechi et al. | 52/169.6 |
| 3,227,061 | 1/1966 | Swayze | 52/169.6 |
| 3,511,162 | 5/1970 | Truhan | 5/362 |
| 3,512,314 | 5/1970 | George et al. | 52/29 |

*Primary Examiner*—Casmir A. Nunberg
*Attorney, Agent, or Firm*—Burns, Doane, Swecker & Mathis

[57] ABSTRACT

The environment of an enclosed space is controlled to simulate the conditions of an arbitrarily selected geographic site. The sound, temperature and light of the space are raised and lowered in accordance with a predetermined program to coincide with the occurrence of dawn and dusk, respectively, at the arbitrarily selected site.

8 Claims, 2 Drawing Figures

Figure 1:
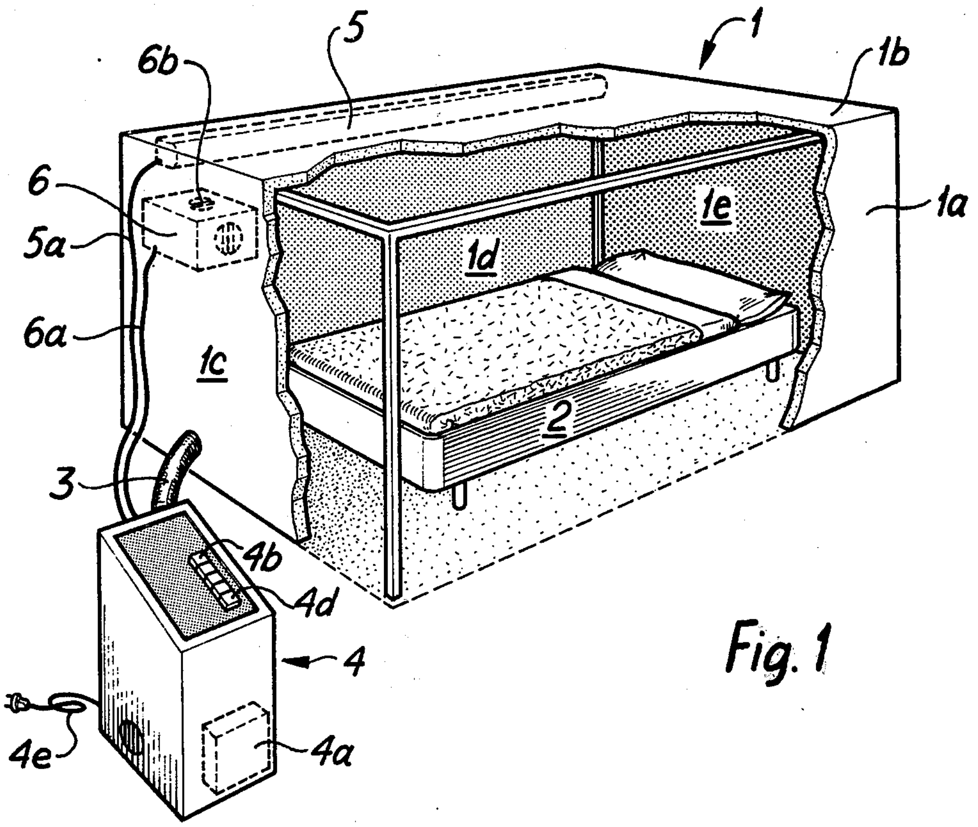

DEFINED SPACE HAVING SOUND-INSULATED AND LIGHT-IMPERMEABLE WALLS, PREFERABLY INTENDED TO ENCLOSE A BED

The present invention relates to a defined space or a cabin having sound-insulated and light-impermeable wall, in which the defined space can be arranged to enclose a bed. When placed in such a defined space, the bed and a person resting thereon is fully secluded from the surroundings with regard to impressions caused by light and vision.

The defined space constructed in accordance with the invention can be used within a multiplicity of different fields. For example such a defined space, hereinafter referred to as a room, can be used by the crews of aircraft intended for intercontinental traffic, which crews are today considerably disturbed as a result of the change occurring in their biological rhythm. This problem can be illustrated by considering the crew of an aircraft flying from Zürich to New York. When the aircraft leaves Zürich for New York, the crew are subjected to a troublesome time difference from the start in Zürich to the landing in New York. If it is assumed that the aircraft leaves Zürich at 12.00 hours time it will land in New York at 14.40 hours local time on the same day, although the local New York time is corresponded by 20.00 hours Zürich-time. In order to maintain the daily rhythm, it is thus necessary for the crew of the aircraft to go to bed to sleep after approximately 2 hours have lapsed. This is extremely difficult, however, since 22.00 hours Zürich-time is corresponded by a New York time of 16.40 hours. At a Zürich-time of 22.00 hours, the crew will therefore be disturbed by noise and light, and also possibly by relatively high room temperatures which prevail in New York.

It is therefore a desired possibility to be able to simulate those light-and sight-impressions and temperatures prevailing in Zürich and corresponding to Zürich time for the crew of such an aircraft. According to one embodiment of the present invention, the crew shall be placed in the aforedescribed room and subjected in said room to those sound and sight impressions which are significant to Zürich at the mentioned Zürich time of 22.00 hours. These significant sound, sight and sensing impressions are generated in special devices arranged within the room, these devices being controlled by a common central control apparatus.

In order for the present invention to be effective, it is important that no noise from without can be heard therein and that light from the surroundings is completely screened from the interior of said room.

The temperature in the room can be controlled and made to correspond to the temperature prevailing in a corresponding room in Zürich, by the arrangement of air-conditioning or climatizing devices connected to the room and controlled by a central control unit. The light-producing means arranged in the room may also be connected to the aforementioned central control unit, and the central control unit may be arranged to generate control signals which cause the light-generating means to generate light corresponding to dusk in Zürich. It will be understood that the central control unit can also be programmed to simulate dawn. This would take place at a time when dawn begins to break in Zürich.

Since the level of sound in the streets etc., normally falls after dusk, it is proposed in accordance with the invention that a sound-generating means is activated by the central control unit so that the sound level drops as the simulated night approaches and, optionally, increases as the simulated dawn breaks.

By means of this arrangement, it is ensured that the crew will sleep soundly under changed conditions and are able to fly from New York to Zürich fully refreshed.

The above described example relating to the problems experienced by Aircraft crews also applies to passengers of aircraft, and particularly those passengers who fly on short trips to a geographically remote place, for example, from Zürich to New York.

The present invention is not restricted to solving the problems of changes in biological rhythm, but can also be applied to reduce the problems in modern building development schemes. It has been found that in the development of towns and cities serious sound problems are created. These problems can not normally be solved unless a very high capital outlay can be accepted. As is well known, houses are often positioned in the vicinity of motorways or airfields. The streets of city centres for example are also noisy because of the traffic moving therein, resulting in a disturbance of the biological rhythm of people in the vicinity. This is primrily due to the fact that silence which is required can not be obtained. In certain parts of the world, the very high summer temperatures experienced often render sleep impossible or difficult. The installation of an air-conditioning system or climatizing system in older houses or hotels is not only very difficult but also very expensive. Moreover, in the majority of air-conditioning systems, the air-ejection nozzles are placed beneath the windows. If a person occupying the room will seclude himself from sound and light, it is normal practice to draw the curtains. This will eliminate, or at least substantially reduce the efficiency of the air-conditioning system.

A defined space according to the invention can be advantageously used to eliminate the aforementioned problems, and, because the defined space is of very small volume, it has the added advantage of requiring but a small amount of power to drive the air-conditioning system. Even in this respect, it is suitable, if not completely necessary, to provide the space with a central control unit for simulating the break of dawn or the fall of dusk and sound variations connected therewith. It would not be necessary, however, to generate a time displacement in relation to the dawns of alternative days.

The invention can also be used in hospitals. In order to restrict building costs and to provide a better supervision of patients, modern hospitals are provided with small rooms intended for two or more patients. Because of the different sicknesses of these patients and the condition of patients immediately after an operation, cause the patient to disturb each other. The patient who can not only stand his own suffering but must also share the suffering of others is negatively affected psychologically with harmful consequences.

A defined space in accordance with the invention can eliminate this disadvantage particularly when said space is movable so that it can be readily pushed over a bed. The defined space can be equipped with instruments and other devices necessary for treating a patient.

The main features of a defined space in accordance with the present invention are set foth in the characterizing clause of the accompanying claims.

Figure 2:
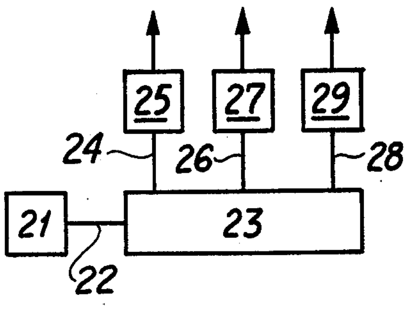

So that the invention will be more readily understood and further features thereof made apparent, an exemplary embodiment of the invention will now be described with reference to the accompanying drawings, in which FIG. 1 is a perspective view, partly in section, of the defined space and a central control unit connected thereto, and FIG. 2 illustrates schematically the components of the central control unit.

The external measurements of the defined space 1 according to the invention are somewhat greater than the external measurements of a bed. The space 1 exhibits sound-insulating and light-impermeable wall members 1*a*, 1*b*, 1*c*, 1*d* and 1*e*, thereby isolating the space completely from surrounding light and sound. These sound-insulating and light-impermeable wall members may comprise a sound-proof textile material coated on the inner and outer sides with a sheet of plastics material.

The bed is referenced 2 in FIG. 1. An air-conditioning system or climatizing system is connected to the space 1 via a line 3, said air-conditioning system or climatizing system being incorporated in a central unit 4. Electrical power is supplied to the unit 4 via a line 4*a*. The central unit 4 comprises a control unit 4*a* in the form of a data device capable of being programmed in a known manner to provide the functions hereinafter described. The function of the data will be described hereinafter. A means 5 for generating light in the space is fixedly arranged on the side wall 1*d* and the roof part 1*b*, said means 5 being connected to said central control unit via a line 5*a* in a manner such that the intensity at which the light is generated can be controlled to correspond to that light intensity experienced at dusk and at dawn. Also arranged within the space is a sound-generating means 6 connected to the central control unit 4*a* by a line 6*a*. The sound-generating means 6 may be provided with a microphone 6*b* to enable the sound generated in the space 1 to be heard. In this way a person resting on the bed may talk to a person located outside the space. The means necessary herefore are previously known and have not been shown for the sake of clarity.

The central control unit 4*a* is arranged to control the temperature in the space 1 via an air-conditioning system (not shown in the Figure) in dependence upon the time, which means that the temperature within the space 1 shall be maintained at a lower level during the night than during the day and evening, and in dependence upon a pre-set program. The air-conditioning system is controlled in a manner such that falls and increases in temperature take place during a pre-determined period of time. The program can be set to simulate temperatures in a room in Zürich, despite the fact that the space 1 is placed in New York, as with the aforegoing example.

The central control unit 4*a* controls the light-generating means 5 in the space 1 to produce light corresponding to dusk and dawn at pre-determined periods of time, beginning from a pre-determined point of time.

This means that when the defined space is placed in New York, the light in the space 1 generated by the means 5 creates a dawn or a dusk effect at a point of time at which dawn and dusk would normally fall in Zürich at a point in time corresponding to the same time in Zürich.

The light-generating means 6 is controlled via the line 6*a* by the central control unit so as to produce a pre-determined level of sound over a pre-determined period of time beginning from a pre-determined point of time. Thus, it is suitable to provide a dawn-light effect whilst at the same time generating a low level of sound via the light-generating means, and to increase the intensity of this sound during the whole of the dawn period.

In a similar manner, the sound-generating means can be caused to reduce its level of sound over the period which the dusk effect is enacted.

In a particularly suitable embodiment, the central control unit can be permitted to activate the light-generating means to create a dusk or dawn effect at points of time which differ from the times at which dusk falls or dawn breaks at the geographic site of the space but coincide with the time at which dusk falls or dawn breaks at an arbitrarily selected geographic site. In this way, the light conditions in the space 1 can be adjusted to the light conditions in Zürich even when the space 1 is located in New York.

A further advantage afforded by the invention is that the central control unit can be caused to activate the air-conditioning system so as to cause the temperature in the space 1 to fall to a level corresponding to night temperatures at points of time which differ from the time prevailing in the geographic site of the space 1 but coincide with the time at which night would fall in an arbitrary selected geographic site, for example Zürich.

Thus, the central control unit, via a program control means, can generate control signals which activate means so that the conditions within the space 1 correspond to the conditions prevailing in a pre-selected geographic site and differing from the geographic site of the space 1.

The central unit 4 is activated by means of a button 4*b*. Returning to the aforegoing example, when the central unit 4 and the define space 1 are placed in New York and one of the aircrew of an aircraft arriving from Zürich intends to rest on the bed 2, the button 4*b* is pressed so as to activate the central control unit 4*a*, which will then produce output signals which simulate in the space 1 the actual conditions in Zürich with the regard to light, sound and temperature.

The central control unit is illustrated in FIG. 2 in simplified form, said control unit being operated by a clock-pulse generator 21 whose pulses are supplied to a control means 23 via a line 22. At a pre-determined time during a pre-determined duration of time, signals are sent via the line 24 to an air-conditioning system 25, these signals controlling the air-conditioning system 25 in the manner to vary the temperature in the defined space 1 independence upon which of the buttons 4*b* to 4*d* is pressed. In a similar manner, the control means 23 sends control signals to a sound-generating means 27, via a line 26, with a variable sound intensity in relation to time, so that said means 27 can generate sound in the sound-generating means 6 with a continuously increasing sound intensity during a simulated dawn but with a continuously decreasing sound intensity during a simulated dusk. Finally, it is shown that the control means can activate the means 5 for generating light in the space 1 via the line 28 and via means 29 so that control signals are sent at a pre-determined point of time and to generate over a pre-determined duration of time a light intensity which corresponds to dusk or dawn. The times at which these control signals are sent and the length of time over which they are sent depends upon the program of the data apparatus. Different programs can be selected by means of the buttons 4*b*–4*d*.

The invention is not restricted to the described and illustrated embodiment but can be modified within the scope of the following claims.

I claim:

1. A defined space having sound-insulated and light-impermeable wall members comprising:
 air conditioning means connected to said space for controlling the atmospheric conditions therein;
 means for generating sound in said space, the intensity of the sound being variable over a predetermined duration of time;
 means for controlling the intensity of the sound generated in said space to simulate the decrease in ambient sound intensity occurring during an evening period and the increase in ambient sound intensity occurring during a morning period; and
 a central unit for producing control signals for said air-conditioning means and said sound generating means to simulate the ambient conditions of a predetermined geographic site.

2. The defined space of claim 1 wherein said central unit produces control signals for said air-conditioning means and said sound generating means to simulate conditions of a predetermined geographic site different from the actual site of said space.

3. The defined space of claim 1 further including means for generating light in said space, wherein said central unit produces a control signal for said light generating means to simulate dawn and dusk in coincidence with the times at which dawn breaks or dusk falls at the actual geographic site of said space.

4. The defined space of claim 1 further including means for generating light in said space, wherein said central unit produces a control signal for said light generating means to simulate dawn and dusk in coincidence with the times at which dawn breaks and dusk falls at an arbitrarily selected geographic site different from the geographic site of said space.

5. A defined space according to claim 1, wherein the central unit comprises a data processor programmed with different programs.

6. A space according to claim 5, wherein the central unit controls the temperature in said space via said air-conditioning means.

7. A space according to claim 1, wherein the sound generating means includes a microphone for sensing the sound generated in said space.

8. A space according to claim 4, wherein the central unit sends control signals to the air-conditioning means to cause said means to reduce the temperature in said space to a level corresponding to night temperatures at points of time which coincide with the time at which night falls in an arbitrarily selected geographic site different from the actual site of said space.

* * * * *